(12) United States Patent
Taylor et al.

(10) Patent No.: US 8,883,131 B2
(45) Date of Patent: Nov. 11, 2014

(54) COMPOSITION FOR THE TREATMENT OF HAIR LOSS AND BALDNESS

(76) Inventors: Robert Peter Taylor, London (GB);
Kartar Singh Lalvani, London (GB);
Ajit Lalvani, Oxford (GB)

( * ) Notice: Subject to any disclaimer, the term of this patent is extended or adjusted under 35 U.S.C. 154(b) by 56 days.

(21) Appl. No.: 12/925,587

(22) Filed: Oct. 26, 2010

(65) Prior Publication Data
US 2011/0070315 A1    Mar. 24, 2011

(51) Int. Cl.
| | | |
|---|---|---|
| *A61Q 7/00* | (2006.01) | |
| *A61K 8/19* | (2006.01) | |
| *A61K 8/27* | (2006.01) | |
| *A61K 8/34* | (2006.01) | |
| *A61K 8/36* | (2006.01) | |
| *A61K 8/37* | (2006.01) | |
| *A61K 8/40* | (2006.01) | |
| *A61K 8/43* | (2006.01) | |
| *A61K 8/46* | (2006.01) | |
| *A61K 8/49* | (2006.01) | |
| *A61K 8/67* | (2006.01) | |
| *A61K 8/97* | (2006.01) | |
| *A61K 8/42* | (2006.01) | |
| *A61K 8/92* | (2006.01) | |

(52) U.S. Cl.
CPC ... *A61Q 7/00* (2013.01); *A61K 8/42* (2013.01); *A61K 8/43* (2013.01); *A61K 8/49* (2013.01); *A61K 8/4926* (2013.01); *A61K 8/671* (2013.01); *A61K 8/922* (2013.01); *Y10S 514/88* (2013.01)
USPC .......... 424/70.1; 424/639; 424/642; 424/682; 424/739; 424/756; 424/760; 514/143; 514/276; 514/345; 514/355; 514/552; 514/564; 514/565; 514/588; 514/625; 514/711; 514/880

(58) Field of Classification Search
USPC ......... 424/760, 639, 641, 642, 682, 692, 697, 424/70.1, 739, 756; 514/880, 143, 276, 514/345, 355, 552, 564, 565, 588, 625, 711
See application file for complete search history.

(56) References Cited

PUBLICATIONS

Olajos, E.J. et al., "Pharmacology/Toxicology of oleoresin capsicum, capsaicin, and capsaicinoids," in: Olajos et al. (eds.), Riot Control Agents. Informa Healthcare, 2004, pp. 123-144.*
Rogers, N.E., "Medical treatments for male and female pattern hair loss," Journal of the American Academy of Dermatology, Oct. 2008, pp. 547-566.*
Sawaya, M.E. et al., "Alopecia: unapproved treatments or indications," Clinics in Dermatology, vol. 18(2), 2000, pp. 177-186.*
Barth, J.H., "Should men still go bald gracefully," The Lancet, vol. 355, Jan. 2000, pp. 161-162.*

* cited by examiner

*Primary Examiner* — John Pak

(57) ABSTRACT

A synergistic composition, or the use of that composition in the manufacture of a medicament, or a method of treatment including the use of that composition, for the treatment of hair loss and baldness, for combined, sequential or simultaneous administration, in any form, via any biological route. In its optimal embodiment the composition consists, in the form of a lotion: 1600-2400 IU/mL Vitamin A Palmitate, 0.64%-0.96% Thiamine Hydrochloride, 0.64%-0.96% Pyridoxine Hydrochloride, 4.8%-7.2% Niacinamide, 2.85%-5.2% D-Panthenol, 1.6%-2.4% L-Arginine, 3.6%-4.4% Methyl Sulphonyl Methane (MSM), 0.08%-0.12% Ginger Oil, 0.08%-0.12% Cinnamon Oil, 0.0996%-0.1494% Oleoresin Capsicum, 1.3%-1.95% Magnesium, 2.4%-3.6% Zinc, 0.192%-0.288% Manganese, 2.6%-3.9% Urea, 2.4%-3.6% Sodium Glycerophosphate, 4.8%-7.2% L-Lysine HCl, plus Preservatives, Co-solvent (Propylene Glycol), Fragrances, Anti-Oxidant, Cooling agent (Menthol), Emulsifier, and Vehicle (Purified water).

2 Claims, No Drawings

COMPOSITION FOR THE TREATMENT OF HAIR LOSS AND BALDNESS

BACKGROUND OF THE INVENTION

This invention concerns a synergistic composition, in the form of a lotion, for the treatment of hair loss and baldness.

Hair undergoes a regular cycle of growth. At any one time, and depending on the age and the sex of the person, up to 90% of hair follicles can be in anagen, the growing phase, and only 10% in telogen, the resting phase, when hairs are normally shed. An alteration in this ratio can lead to an increased rate of hair loss and thus an impression of impending baldness. Baldness involves the state of lacking hair where it often grows, especially on the head. The most common form of baldness is a progressive hair thinning condition called androgenic alopecia, which is also called androgenetic alopecia, male pattern baldness or female pattern baldness. The severity and nature of baldness can vary greatly, from male and female pattern alopecia. Hair loss is a common disorder that affects men and women of all ages. About 50% of men and women suffer from hair loss by the age of 40. Excessive falling hair, baldness and unhealthy looking hair can be a result of several factors including: age and genetic factors, inadequate nutrition, hormonal imbalance, medical disorders such as cancer and anaemia, certain types of medication and chemotherapy, environmental factors such as pollution, trauma and stress, rapid weight loss, infections, and improper hair care. Many of the hair loss remedies available today rely on synthetic xenobiotic chemicals may contain some components as the primary active. Such products give only temporary relief. Application of temporary and harmful chemicals are not an ideal scenario for the hair disorders, which need a solution that can be used over the lifetime of the individual. Certain nutritional components can provide some effective, long term, and easy to use remedies.

Having healthy hair and a healthy scalp begins with proper nutritional building blocks. The hair follicle is highly active, and so the metabolic requirements for oxygen, energy and protein synthesis must be met to maintain healthy hair. A reduction of nutrients in, the diet or a reduction of blood supply to the scalp can threaten the delivery of adequate oxygen, glucose and essential nutrients. These issues are compounded by the ageing process, which has a negative impact on the body's ability to assimilate nutrients required to maintain normal physiological hair condition. Topical nutritional application can therefore bypass age related reductions in absorption and microcirculatory reductions, and so directly safeguard the nutritional environment of the hair follicle.

BRIEF SUMMARY OF THE INVENTION

This lotion has been developed for men and women who want to counteract hair loss and poor scalp health, and for those who want to improve their hair growth and condition. It has been formulated to provide a complete spectrum of hair nutrients, amino acids, and special plant derived nutrients, that play a role in scalp health and the metabolism of the hair follicle, and that support healthy growth of hair. Benefits are delivered directly at the hair root.

According to this invention, there is a synergistic composition, or the use of that composition in the manufacture of a medicament, or a method of treatment including the use of that composition, for the treatment of hair loss and baldness, for combined, sequential or simultaneous administration, in any form, via any biological route. In its optimal embodiment the composition consists, in the form of a lotion of: 1600-2400 IU/mL Vitamin A Palmitate, 0.64%-0.96% Thiamine Hydrochloride, 0.64%-0.96% Pyridoxine Hydrochloride, 4.8%-7.2% Niacinamide, 2.85%-5.2% D-Panthenol, 1.6%-2.4% L-Arginine, 3.6%-4.4% Methyl Sulphonyl Methane (MSM), 0.08%-0.12% Ginger Oil, 0.08%-0.12% Cinnamon Oil, 0.0996%-0.1494% Oleoresin Capsicum, 1.3%-1.95% Magnesium, 2.4%-3.6% Zinc, 0.192%-0.288% Manganese, 2.6%-3.9% Urea, 2.4%-3.6% Sodium Glycerophosphate, 4.8%-7.2% L-Lysine HCl, plus Preservatives, Co-solvent (Propylene Glycol), Fragrances, Anti-Oxidant, Cooling agent (Menthol), Emulsifier, and Vehicle (Purified water).

DETAILED DESCRIPTION OF THE INVENTION

This invention concerns a synergistic composition, in the form of a lotion, for the treatment of hair loss and baldness.
The following is the optimal formulation of the lotion:—
Vitamin A Palmitate: 1600-2400 IU/mL
Thiamine Hydrochloride: 0.64%-0.96%
Pyridoxine Hydrochloride: 0.64%-0.96%
Niacinamide: 4.8%-7.2%
D-Panthenol: 2.85%-5.2%
L-Arginine: 1.6%-2.4%
Methyl Sulphonyl Methane (MSM): 3.6%-4.4%
Ginger Oil: 0.08%-0.12%
Cinnamon Oil: 0.08%-0.12%
Oleoresin Capsicum: 0.0996%-0.1494%
Magnesium: 1.3%-1.95%
Zinc: 2.4%-3.6%
Manganese: 0.192%-0.288%
Urea: 2.6%-3.9%
Sodium Glycerophosphate: 2.4%-3.6%
L-Lysine HCl: 4.8%-7.2%
Plus the following:
Preservatives
Co-solvent (Propylene Glycol)
Fragrances
Anti-Oxidant
Cooling agent (Menthol)
Emulsifier
Vehicle (Purified water)
Relevance of the Constituents:

Vitamin A Palmitate is an antioxidant that helps to produce healthy sebum in the scalp.

Thiamine Hydrochloride helps to give hair shine and good texture.

Pyridoxine Hydrochloride prevents hair loss, and helps to create melanin, which gives hair its colour.

Niacinamide promotes scalp circulation.

D-Panthenol prevents graying and hair loss.

L-Arginine promotes scalp hair growth.

Methyl Sulphonyl Methane (MSM) contains sulphur, which is required for the production of keratin and collagen. Both are important constituents of hair.

Ginger Oil has a soothing effect.

Cinnamon Oil is a natural astringent.

Oleoresin Capsicum stimulates hair growth by as much as 50%, and increases blood flow to the scalp, as well as histamine release in order to stimulate cell division. Capsaicin might act by increasing IGF-I production in hair follicles in the skin. Effects might be mediated by sensory neuron activation in the skin.

Magnesium works with calcium to promote healthy hair growth.

Zinc works together with Vitamin A. A deficiency in either can lead to dry hair and oily skin.

Manganese prevents slow hair growth.

Urea is an emollient (a skin softening agent). Urea enhances penetration kinetics of vitamin A into the various layers of human skin. Urea may also help to soften thick scalp plaques. Urea is also a source of nitrogen for hair growth.

Sodium Glycerophosphate is a buffering agent.

L—Lysine HCl increases iron stores and decreases hair loss by one half.

Uses
1. To maintain healthy hair follicles
2. To reactivate and regenerate hair follicles
3. To allow fresh healthy hair growth. Visible effect of fresh hair growth may be noticeable within two months.
4. To maintain healthy scalp condition
5. To reduce diffuse hair loss and baldness.

Mode of Action
1. Provides nourishment and strengthens hair
2. Protecting the hair and scalp from free radical damage Instructions for Application
1. Massage the lotion liberally on the affected bald area or diffuse hair loss area or throughout scalp to reduce abnormal hair loss and improve scalp condition.
2. Use a dropper to deliver the lotion on the scalp. While delivering it, gently massage it into the applied area for about a minute.
3. Leave it on for 6-8 hours then wash it off with a good shampoo.
4. Keep this medicine away from the eyes. If you accidentally get some in your eyes, flush them thoroughly with water.

Safety

The lotion is safe when applied topically. It has not been reported to cause any known skin irritation or allergic reactions.

Manufacturing Instructions

I Aqueous Phase
1. Add Water Purified to a suitable manufacturing tank. And heat to 90° C. 100° C.
2. Add the preservatives—Parabens and stir to dissolve. Check the clarity of the solution and proceed. Stop heating.
3. Cool the solution to about 70° C. Add and dissolve under stirring, the following in sequence, whilst maintaining the temperature at about 70° C.:
   a. Magnesium Sulphate
   b. Zinc Sulphate
   c. Urea
   d. Manganese sulphate
   e. Methyl Sulphonyl Methane (MSM)
   f. L-lysine
   g. Sodium Glycero Phosphate
4. In a suitable separate tank, take purified water and warm it to about 75° C. Add L-Arginine under stirring and dissolve. Check the clarity. Add the clear solution to the main manufacturing tank while the bulk is being stirred in the Step I-4.
5. Cool the mixed solution in the main manufacturing tank to 40° C. to 45° C.
6. Add the following in the order, under stirring to dissolve:
   a. Nicotinamide
   b. Vitamin B1
   c. Vitamin B6
   d. D-Panthanol
Check clarity before proceeding.

II Aqueous Phase
1. To a suitable dry mixing tank add the following in order, and mix to uniformity:
   a. Oil Lemon
   b. Oil Orange
   c. Oil Ginger
   d. Cinnamon Oil
   e. Oleoresin Capsicum 2. Add to the oil mixture in Step II-1 and then dissolve by stirring, the Antioxidants—Butylated Hydroxy Anisole (BHA) and Butylated Hydroxy Toluene (BHT).
3. Add Menthol to the oils and stir to dissolve. Check for completeness of the solution.
4. Add Vitamin A to the above oils and mix to uniformity.
5. In a dry, separate mixing tank, add Polyoxyl-40-Hydrogenated Castor Oil. Warm it if required to 45° C. and then cool it to room temperature, not more than 30° C. Add above oil mixture containing Menthol and Vitamin A. Mix it to clarity.

III Main Mixing
1. Add the Oil phase from Step II-5 slowly in a thin stream to the Aqueous phase in the main manufacturing tank, in Step I-6.
2. Add a sufficient purified water to make up the batch and mix to uniformity.
3. Filter the batch through a suitable filter medium.

IV Filling
1. Fill the appropriate volume per container and then seal the cap. Appropriately label individual sealed container and pack.

Batch Manufacturing Process
1. In a clean, dry, and approved main stainless steel tank, add the vehicle and heat it. Boil and then add preservatives and continue boiling to get a clear solution.
2. Add the Magnesium, Zinc, Manganese, Urea, Methyl Sulphonyl Methane, L-Lysine Hydrochloride, and Sodium Glycerophosphate in the main stainless steel tank. Check the clarity of the solution.
3. In a separate clean, dry and approved stainless steel tank, add vehicle and dissolve L-Arginine in it. Heat it if necessary and add this solution to the main tank.
4. Add the Niacinamide, Vitamin B6, Vitamin B1, D-Panthenol in the main tank and dissolve.
5. Add the co-solvent in main bulk and mix for 10 minutes. Filter the solution through 200 mesh nylon cloth.
6. Add fragrances, antioxidant, cooling agent, soothing agent, astringent and Vitamin A in a clean, dry and approved stainless steel tank. Mix it well to get a clear solution.
7. In a separate clean, dry and approved stainless steel tank add Polyoxyl-40-Hydrogenated Castor Oil. Add the materials from Step 6 into Step 7. Mix it well.
8. Add materials from step 7 into the main stainless steel tank. Mix it for 15 minutes.
9. Filter the final solution through 100 mesh nylon cloth.

Progressively more concise but lesser versions of the invention could include: Urea, Methyl Sulphonyl Methane, L-Arginine, Oleoresin Capsicum, D-Panthenol, and one or two or more of Vitamin A Palmitate, Thiamine Hydrochloride, Pyridoxine Hydrochloride, Niacinamide, Ginger Oil, Cinnamon Oil, Magnesium, Zinc, Manganese, Sodium Glycerophosphate, L-Lysine HCl; or could comprise: Urea, Methyl Sulphonyl Methane, L-Arginine, Oleoresin Capsicum.

The invention claimed is:

1. A composition in the form of a lotion for improving scalp health comprising 1600-2400 IU/ml Vitamin A Palmitate, 0.64%-0.96% Thiamine Hydrochloride, 0.64%-0.96% Pyridoxine Hydrochloride, 4.8%-7.2% Niacinamide, 2.85%-5.2% D-Panthenol, 1.6%-2.4% L-Arginine, 3.6%-4.4% Methyl Sulphonyl Methane, 0.08%-0.12% Ginger Oil, 0.08%-0.12% Cinnamon Oil, 0.0996%-0.1494% Oleoresin Capsicum, 1.3-1.95% Magnesium, 2.4%-3.6% Zinc, 0.192%-0.288% Manganese, 2.6%-3.9% Urea, 2.4%-3.6% Sodium Glycerophosphate, 4.8%-7.2% L-Lysine HCl, as active ingredients, and further comprising: Preservatives, Propylene Glycol, Fragrances, Anti-Oxidant, Menthol, Emulsifier, and Purified Water.

2. A composition in the form of a lotion for improving scalp health comprising 1600-2400 IU/ml Vitamin A Palmitate, 0.64%-0.96% Thiamine Hydrochloride, 0.64%-0.96% Pyridoxine Hydrochloride, 4.8%-7.2% Niacinamide, 2.85%-5.2% D-Panthenol, 1.6%-2.4% L-Arginine, 3.6%-4.4% Methyl Sulphonyl Methane, 0.08%-0.12% Ginger Oil, 0.08%-0.12% Cinnamon Oil, 0.0996%-0.1494% Oleoresin Capsicum, 1.3-1.95% Magnesium, 2.4%-3.6% Zinc, 0.192%-0.288% Manganese, 2.6%-3.9% Urea, 2.4%-3.6% Sodium Glycerophosphate, 4.8%-7.2% L-Lysine HCl.

\* \* \* \* \*